United States Patent
Heine et al.

(10) Patent No.: US 7,441,282 B2
(45) Date of Patent: Oct. 28, 2008

(54) HEADBAND APPARATUS FOR HEAD-WORN OPTICAL INSTRUMENTS

(75) Inventors: Helmut Heine, Diessen (DE); Oliver Heine, Herrsching (DE); Anton Schneider, Munich (DE)

(73) Assignee: Heine Optotechnik GmbH & Co. KG, Herrsching (DE)

( * ) Notice: Subject to any disclaimer, the term of this patent is extended or adjusted under 35 U.S.C. 154(b) by 282 days.

(21) Appl. No.: 11/354,991

(22) Filed: Feb. 16, 2006

(65) Prior Publication Data

US 2006/0245175 A1 Nov. 2, 2006

(30) Foreign Application Priority Data

Apr. 29, 2005 (DE) .................. 20 2005 006 892 U

(51) Int. Cl.
*A42B 1/22* (2006.01)
(52) U.S. Cl. .......................................................... 2/418
(58) Field of Classification Search .............. 2/6.2, 2/422, 453, 416, 418; 351/158, 205; 359/407, 359/409
See application file for complete search history.

(56) References Cited

U.S. PATENT DOCUMENTS

| | | | | |
|---|---|---|---|---|
| 2,659,266 A | * | 11/1953 | Swisher | 351/227 |
| 4,637,699 A | * | 1/1987 | Sigelman | 351/205 |
| 4,681,413 A | * | 7/1987 | Schmidt et al. | 351/205 |
| 5,412,811 A | * | 5/1995 | Hildenbrand et al. | 2/10 |
| 6,181,413 B1 | | 1/2001 | Manian | |

FOREIGN PATENT DOCUMENTS

| | | |
|---|---|---|
| DE | 28 02 940 C2 | 7/1978 |
| DE | 91 12 377 U1 | 1/1992 |
| DE | 200 06 333 U1 | 6/2001 |
| GB | 2 053 502 A | 2/1981 |
| GB | 2 123 166 A | 1/1984 |
| WO | 89/02202 A1 | 3/1989 |

* cited by examiner

*Primary Examiner*—Katherine Moran
(74) *Attorney, Agent, or Firm*—Rothwell, Figg, Ernst & Manbeck

(57) ABSTRACT

A headband apparatus for head-worn optical instruments includes a headband (12) and a bow (16) on which the optical instrument is fitted, and which is fitted with both its ends (100) to the middle region of the headband (12) such that it can swivel about a swivel axis (S) between a working position and a rest position. Fastening elements (26, 28) for releasably fastening additional elements (38) are fitted on the headband (12).

9 Claims, 6 Drawing Sheets

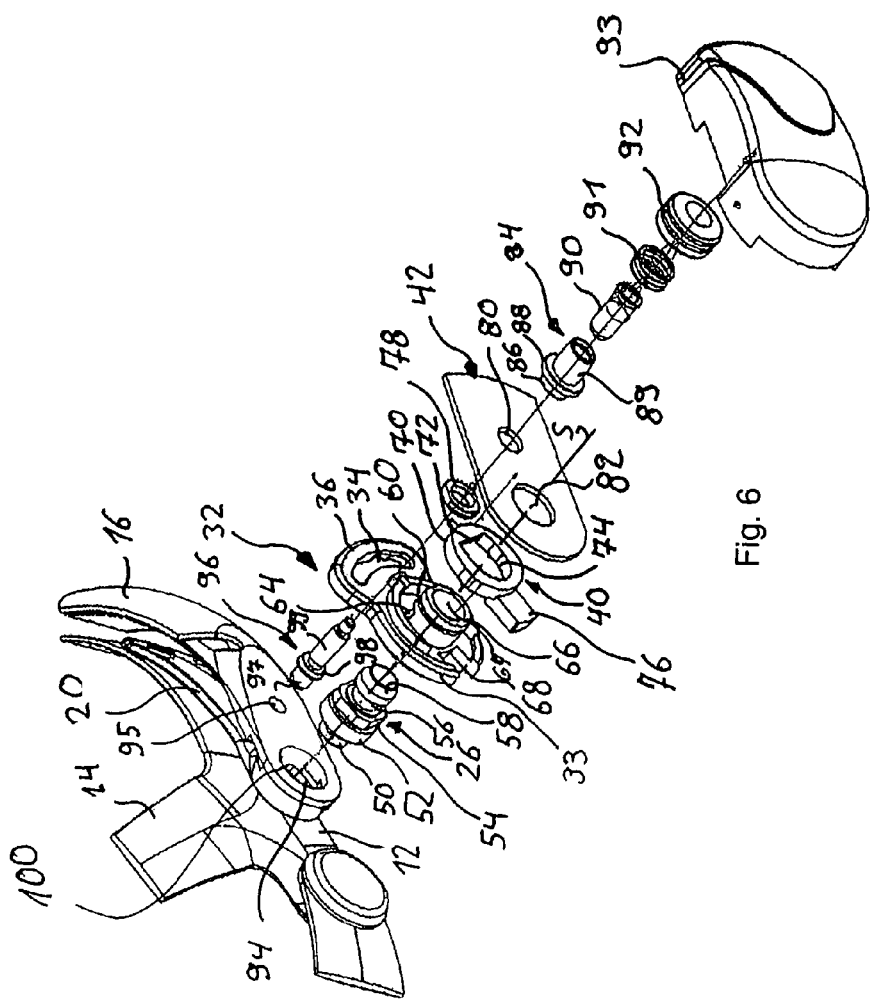
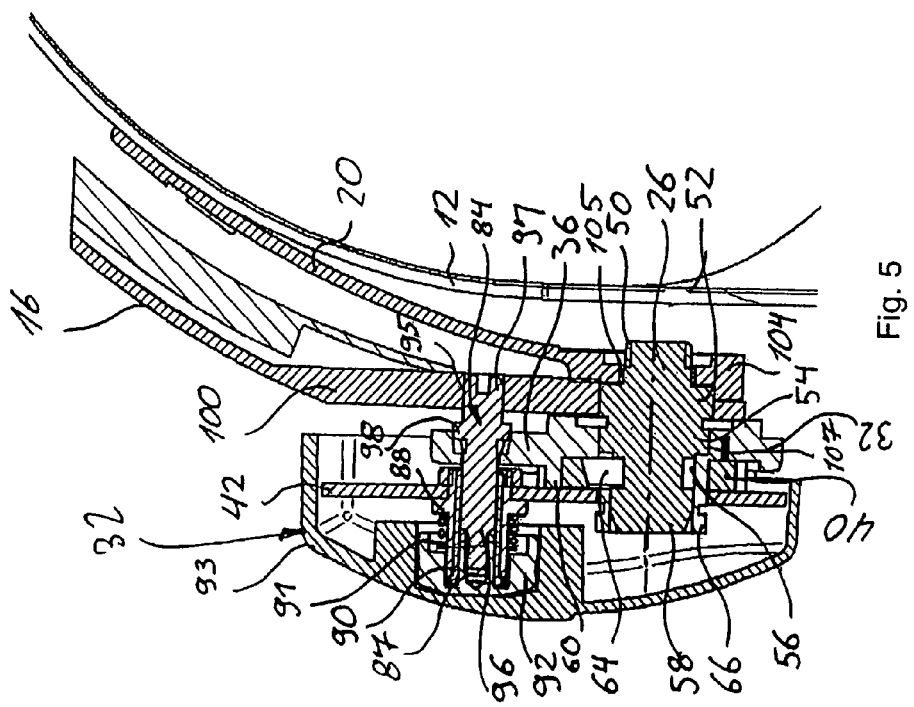

HEADBAND APPARATUS FOR HEAD-WORN OPTICAL INSTRUMENTS

BACKGROUND OF THE INVENTION

1. Field of the Invention

The invention relates to a headband apparatus for an optical instrument comprising a headband and a bow on which said optical instrument is mounted, said bow being mounted with both ends thereof at a middle region of said headband for swiveling about a swivel axis between a working position and a rest position.

2. Description of the Background Art

Such a headband apparatus known from U.S. Pat. No. 4,681,413 comprises an elastic headband surrounding the forehead and back of the head, and a crown band permanently connected thereto. The headband and the crown band can be adapted to the size and shape of the wearer's head with the aid of adjusting apparatuses. A bow is swivelably supported with its two ends in the middle side region of the headband. A binocular ophthalmoscope is fastened on the front side of the bow. The bow can be swiveled upward from a substantially horizontal working position, in which the ophthalmoscope is located in front of an examiner's eye into a rest position in which the ophthalmoscope is brought completely out of the examiner's field of view. Provided at one of the two swivel axes for the purpose of swiveling the bow is a latching device with two stops into which the bow latches in the working position or the rest position. The latching device has an operating element after the activation of which the bow can be unlocked and moved into the appropriate position. The latching device is permanently mounted on the swivel axis of the bow. This means that each examiner, whether a left- or right-hander must use the latching device, arranged on the side of the headband, in order to set the bow. If the latching device is arranged for right-handers, as is normally the case, this constitutes a substantial impairment of the operating comfort for a left-hander. For this reason, the manufacturer finds it necessary to make separate headband apparatuses available both for left-handers and right-handers, thus giving rise to substantial outlay on development and production. Moreover, the known headband apparatus does not provide any additional devices for fastening supplementary apparatuses or units. Finally, the bow is held in the working position at only one end by the latching device. Consequently, the bow is inclined downward in the direction of the other end because of the weight of the ophthalmoscope.

SUMMARY OF THE INVENTION

The invention is therefore based on the object of providing a headband apparatus capable of universal use with the aid of simple means in terms of construction.

This object is achieved according to the invention by a headband apparatus for a head-worn optical instrument, comprising a headband and a bow on which said optical instrument is mounted, said bow being mounted with both ends thereof at a middle region of said headband for swiveling about a swivel axis between a working position and a rest position, wherein fastening elements for releasably fastening at least one additional element are provided on said headband.

According to the invention, fastening elements for releasably fastening additional elements are mounted on the headband. The field of use can be substantially expanded thereby.

If the fastening elements form the swivel axes of the bow and extend outward through the ends of the bow, it is possible, for example, for a latching device to be mounted on one of the fastening elements in a rotationally fixed fashion by form-fitting engagement.

The latching device can include a latching disk which is connected to the fastening element in a rotationally fixed fashion and has a circularly arcuate guide slot in which there is guided a latching pin which is connected to the bow in a rotationally fixed fashion and engages in a latching fashion in the guide slot in the working position and/or the rest position of the bow.

A further additional element, for example a controller for controlling the brightness of a light source, drive electronics for a light source, a camera etc. can be mounted on another fastening element.

Since the latching device is releasably fastened, it can be mounted on both sides of the head. This enables the latching device to be mounted on a side preferred for left handers or right handers.

In a preferred embodiment, the fastening elements are respectively fastened at a free end of a connecting lug whose other end is permanently connected to the headband. The bow is thereby decoupled from the headband.

The fastening element preferably passes through the latching disk and has a circumferential groove in which there engages in a locking position a locking element which is arranged in the latching disk and can be displaced transverse to the swivel axis into a release position in which it is disengaged from the circumferential groove. The locking element is expediently prestressed in the direction of the locking position. When the locking element is displaced into the release position, the complete latching device can be withdrawn from the fastening element and, if necessary, pushed on to the other fastening element and locked with the latter.

BRIEF DESCRIPTION OF THE DRAWINGS

An exemplary embodiment of the invention is explained in more detail below with the aid of drawings, in which:

FIG. 5 shows a section through the bearing of the bow and the latching device, FIG. 6 shows an exploded illustration of the latching device.

DETAILED DESCRIPTION OF THE PREFERRED EMBODIMENTS

Figure 1:
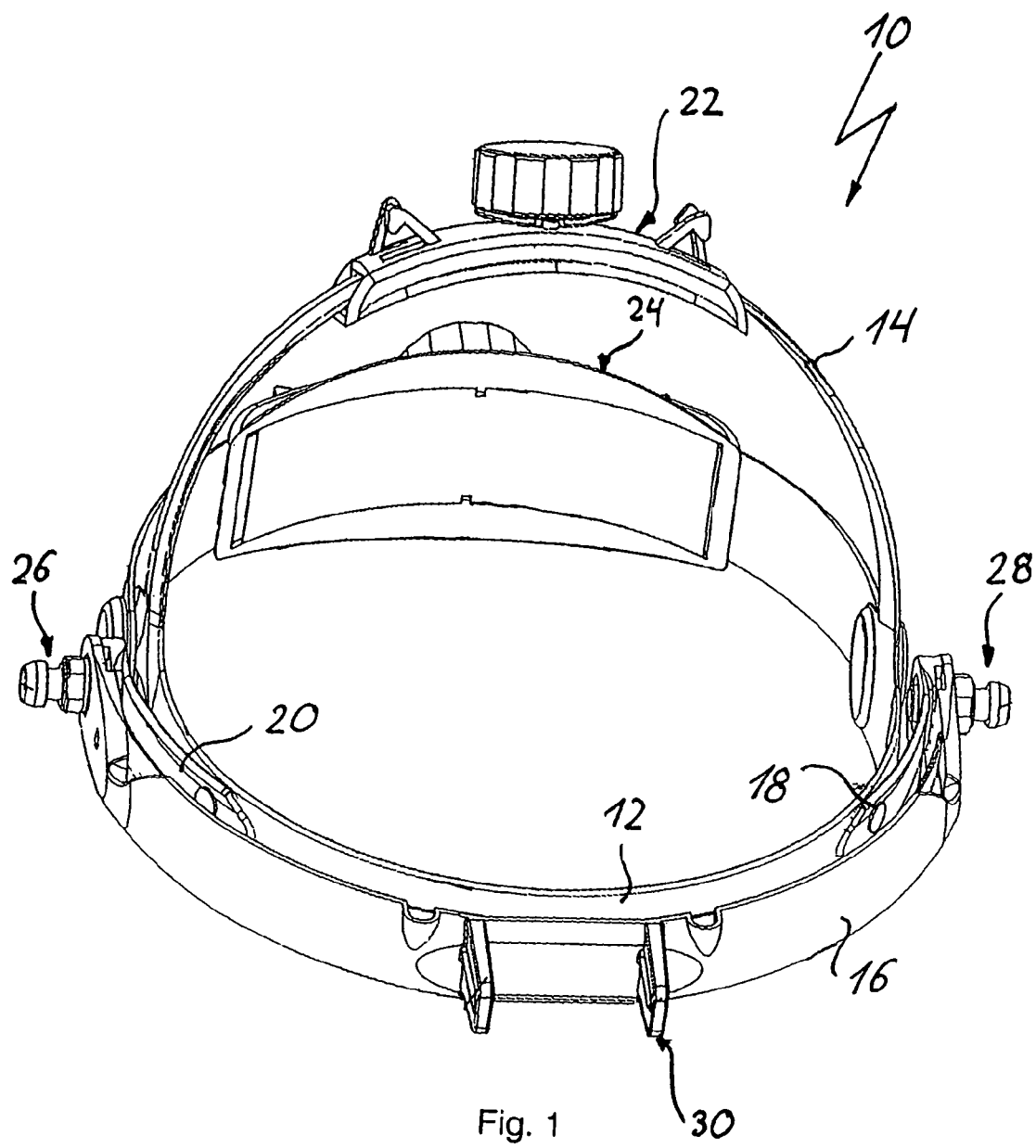
FIG. 1 shows a perspective illustration of a headband apparatus.
Figure 2:
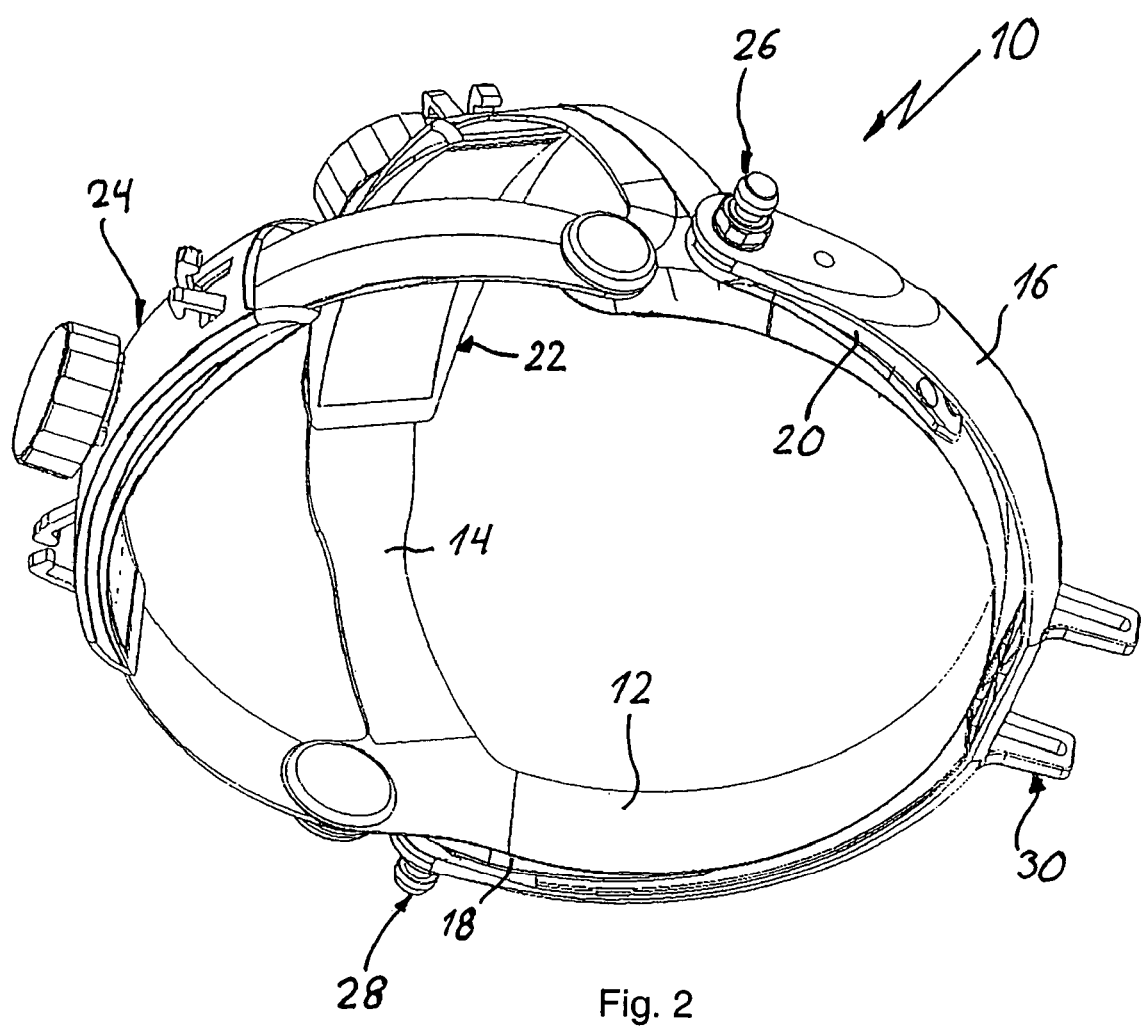
FIG. 2 shows an oblique bottom view of the headband apparatus of FIG. 1.

The headband apparatus 10 shown in FIGS. 1 and 2 comprises a headband 12 that can be adjusted by an adjusting device 24 and of which a crown band 14, which can be adjusted by an adjusting device 22, extends upward. In the front region, surrounding the user's forehead, of the headband 12, connecting lugs 18, 20 are fastened on both sides at one end and extend to the respective middle region of the side. At the free end of the connecting lugs 18, 20, one end of a bow 16 is swivelably supported in each case by fastening elements 26, 28. In the position shown in FIGS. 1 and 2, the bow 16 is located in a substantially horizontal position in which it surrounds the front region of the headband 12. A fastening device 30 for fastening an ophthalmoscope is provided at the middle region of the bow 16.

The bow 16 is formed by a molded plastic part, the electric supply cables being integrated in the bow.

Figure 3:
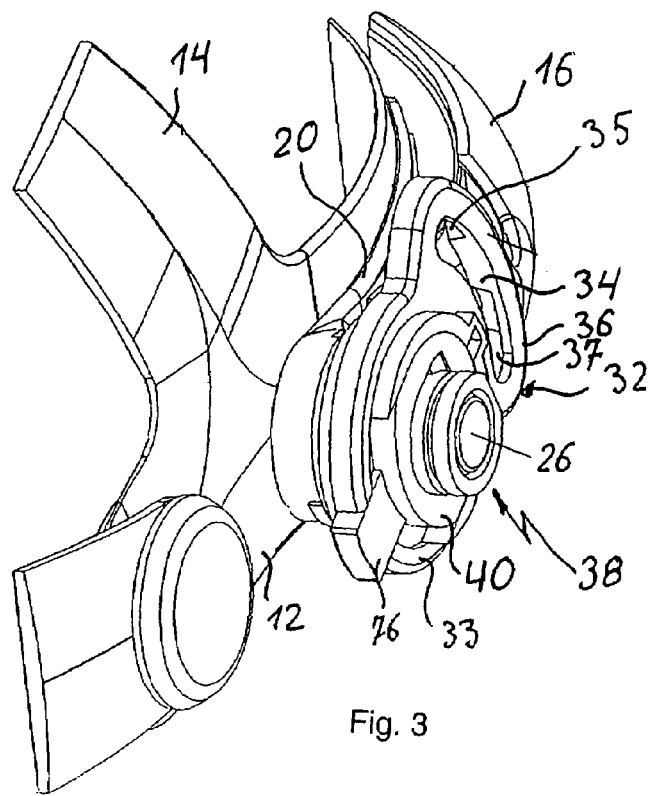
FIG. 3 shows a perspective partial view of the headband apparatus of FIG. 1 in the region of the articulation of a bow with a partially mounted latching device.
Figure 4:
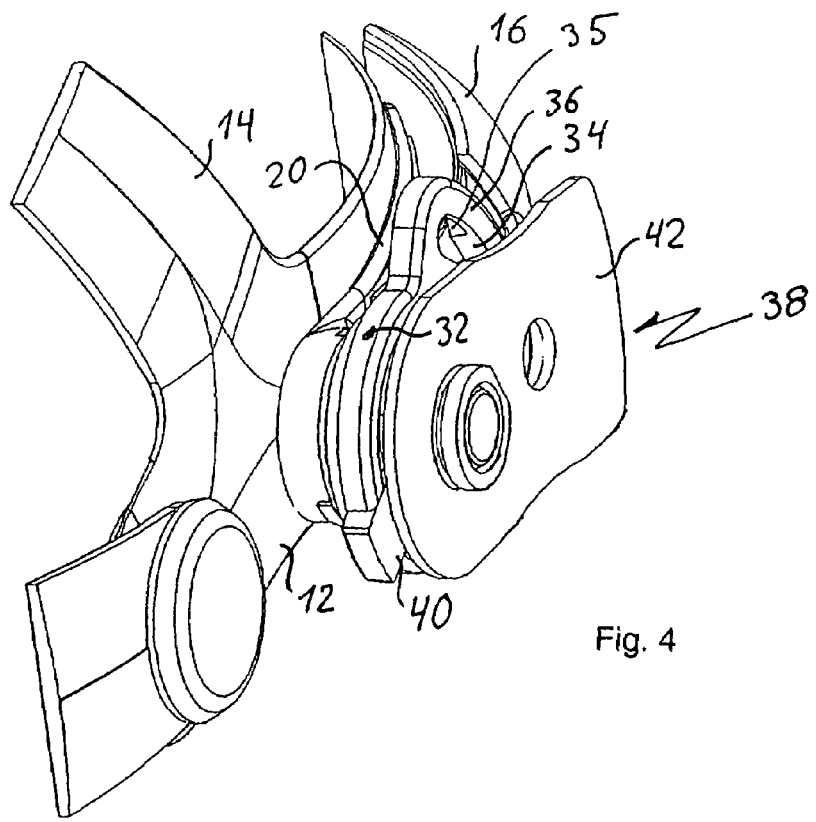
FIG. 4 shows the view of FIG. 3, a swivel plate additionally being mounted.

FIGS. 3 and 4 show perspective illustrations of the headband apparatus 10 in the region of the bearing of the bow 16 by the fastening element 26. FIG. 5 shows a sectional illustration of the bearing with a latching device 38, while FIG. 6 shows an exploded illustration in this region.

The free end of the connecting lug 20 has a thickened end 104 with a passage opening 105. The fastening element 26 with a threaded shoulder 50 passes through this passage opening 105 in the direction of the headband 12. On the side of the thickened section 104 averted from the headband 12, a cylindrical bearing section 52 bears against the fastening element 26. Adjoining the bearing section 52 in the direction of the headband 12 is a square profile 115 (FIG. 9) that is arranged in a square opening 111 (FIG. 9) of the thickened section 104 in order to fit the fastening element 26 on the fastening lug 20 in a rotationally fixed fashion. The fastening element 26 is permanently connected to the connecting lug 20 by a nut (not shown) mounted on the threaded shoulder 50 adjoining the square profile 115. At its thickened end 100, the bow 16 has a continuous bearing opening 94 that surrounds the bearing section 52 of the fastening element 26, such that the bow 16 is supported at the bearing section 52 such that it can rotate about a horizontal swivel axis S. Bearing against the side, averted from the headband 12, of the thickened end 100 of the bow 16 is a latching disk 32 that has an extension 36 extending forward in a substantially horizontal fashion. A circularly arcuate guide slot 34 is formed in the extension 36, the center of the circular arc lying on the swivel axis S of the bow 16, which coincides with the central axis of the fastening element 26 and the through openings 94 and 105. The fastening element 26 passes through a polygonal opening 107 (for example square opening) in the latching disk 32, the profile of which corresponds to the outer profile of a polygonal section 54 of the fastening element 26, as a result of which a rotationally fixed connection is produced between the latching disk 32 and the fastening element 26. Adjoining the polygonal opening 107 is a cylindrical section 66 of the latching disk 32 that is flush with the fastening element 26. The cylindrical section 66 is surrounded at a distance in the front region by a wall 60 formed in the latching disk 32. Provided in the cylindrical section 66 in a fashion facing the wall 60 is a cutout 64 that is at the level of a circumferential groove 56 that is formed in the fastening element 26. A swivel plate 42 with its through opening 82 is pushed on to the cylindrical section 66 in a fashion adjoining the wall 60 and the cutout 64.

Inserted between the swivel plate 42 and the latching disk 32 is a blocking slide 40 that has a through opening 74 through which the cylindrical section 66 passes. The blocking slide 40 surrounds the cylindrical section 66 at the level of the cutout 66 and the wall 60. Adjoining the cutout 64 in the cylindrical section 66, the through opening 74 has a straight circumferential edge 72 that engages in the cutout 64 and in the circumferential groove 56 in the fastening element 26 when the blocking slide 40 is moved rearward transversely to the swivel axis S, that is to say away from the wall 60. The latching disk 32 is thereby locked on the fastening element 26. The blocking slide 40 is prestressed into the locking position by a spring (not shown) arranged between the wall 60 and the blocking slide 40. When, by exerting pressure on a pressure part 76, arranged displaceably in an incision 68 in the latching disk 32, of the blocking slide 40, the blocking slide 32 is moved forward against the pressure force of the spring, the edge 72 is moved out of the circumferential groove 56 in the fastening element 26, as a result of which the latching disk 32 is unlocked from the fastening element 26, and the entire latching device 38 can be withdrawn.

The swivel plate 42 extends forward perpendicular to the swivel axis S of the bow 16. Provided in the front region is a journal opening 80 that is flush with an insertion opening 95 in the thickened end 100 of the bow and is at the level of the guide slot 34. A bush sleeve 84 is guided with a threaded neck 86 through the journal opening 80 and fastened on the swivel plate 42 by means of a nut 78. The bush sleeve 84 bears against the swivel plate 42 with a collar 88 from which a cylindrical section 89 extends outward. Plugged from outside into the bush sleeve 84 is a bearing bush 90 into which there is inserted a cylindrical section 99 of a latching pin 96 that passes through the guide slot 34 and has a plug-in section 97 that is displaceably inserted into the plug-in opening 95. Formed on the latching pin 96 between the latching disk 32 and the thickened section 100 of the bow 16 is a conical collar 98 whose shape is conformal with the shape of latching depressions 35, 37 in the guide slot 34 that correspond to a rest position or working position of the bow 16 and are formed at the upper end or lower end of the guide slot 34. A pressure head 92 is displaceably mounted on the outer end of the bush sleeve 84, a helical pressure spring 91 being provided between the collar 88 of the bush sleeve 84 and the pressure head 92. The pressure head 92 is screwed with the aid of a thread 87 of the latching pin 96. A cap 93 that covers the entire latching device 38 from outside is mounted on the pressure head 92 from outside.

When a pressure is exerted on the cap 93 in the direction of the bow 16, the latching pin 96 is moved via the pressure head 92 against the pressure force of the pressure spring 91 in the direction of the bow 16 until the conical collar 98 bears against the thickened end 100 of the bow 16. In this position, the conical section 98 is located outside the corresponding depression 35 or 37 in the guide slot 34 in the latching disk 32, thereby rendering it possible for the latching pin 96 to move inside the guide slot 34 as the swivel plate 42 swivels in a circular track about the swivel axis S, the bow 16 being carried along by the plug-in section 97, plugged into the plug-in opening 95, of the latching pin 96, and is swiveled about the swivel axis S. As soon as the conical section 28 reaches the other depression 35 or 37, the conical section 98 snaps into the corresponding depression 35 or 37 by the action of the pressure spring 91, the bow 16 thereby being locked.

The entire latching device 38 including the latching disk 32, blocking slide 40, swivel plate 42, latching pin 96, cap 93 etc. can be withdrawn from the fastening element 26 when a pressure force is exerted on the blocking slide 40 in the direction of the swivel axis S, and the edge 72 is moved therethrough out of the circumferential groove 56 in the fastening element 26. The latching device 38 is then withdrawn from the fastening element 26 and can be plugged in the same way on to the identically designed fastening element 28 on the opposite side of the headband 12, the other end of the bow 16 being designed in the same way as the end described.

Figure 7:
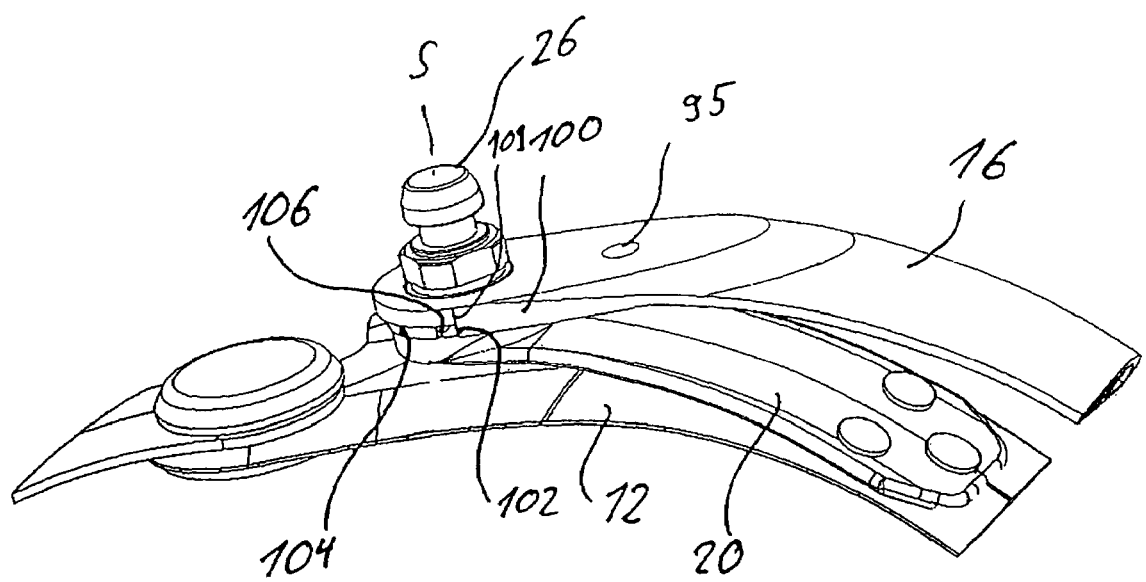
FIG. 7 shows perspectively a partial excerpt of the headband apparatus of FIG. 1 in the region of the bearing of a bow.
Figure 8:
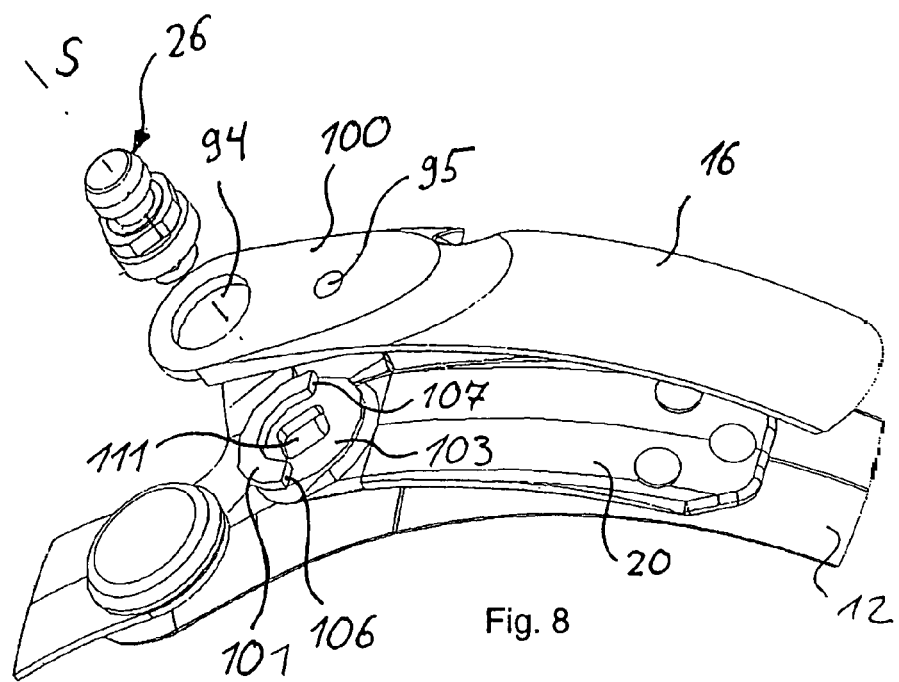
FIG. 8 shows an exploded illustration of the partial excerpt of FIG. 7, seen from outside.
Figure 9:
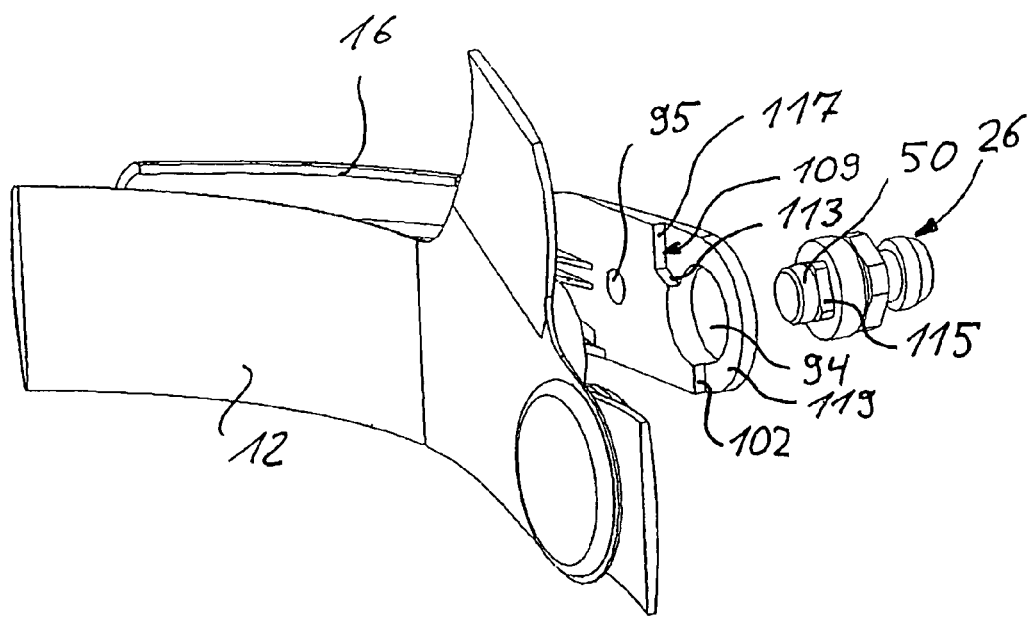
FIG. 9 shows an exploded illustration of the partial excerpt of FIG. 7, seen from inside.

FIGS. 7, 8 and 9 show an enlarged perspective partial excerpt of the headband apparatus 10 in the region of the articulation of an end of the bow 16. At its thickened end 104, the connecting lug 20 has a rearwardly extending semicircular elevation 101 that concentrically surrounds the square opening 111 and projects outward from a bearing surface 103 of the thickened end 104. The elevation 101 finishes above in a stop surface 107, and below in a stop surface 101, both of which point forward and lie in a substantially vertical plane that intersects the swivel axis S.

Provided at the thickened end 100 of the bow 16 is an oppositely arranged step 109 that merges at the bottom, via a rearwardly pointing stop surface 102, into a bearing surface 119 that bears against the top side of the elevation 101. The stop surface 102 extends radially downward from the edge of the bearing opening 94 and bears against the stop surface 106 of the connecting lug 20 when the bow 16 is in the substantially horizontal working position. Formed in the upper region is a substantially vertically arranged step surface 117 that runs perpendicular to the bearing surface 119 and is arranged at a distance in front of the bearing opening 94. Adjoining the step surface 117 is a bearing surface 113 that runs obliquely downward in the direction of the midpoint of the bearing opening 94 and finishes at the edge of the bearing opening 94. The stop surface 113 is arranged such that it bears against the bearing surface 107 of the connecting lug 20 when the bow 16 is swiveled upward into the rest position.

Corresponding stop surfaces 102, 113, 106, 107 are provided at both ends of the headband 12 on the bow 16 and/or the connecting lug 20.

The fact that the stop surfaces 102, 106 bear at both ends in the horizontal position of the bow 16 prevents the bow 16 from being inclined at one end through the weight of the ophthalmoscope fastened on the fastening device 30 when it is locked in the horizontal position at the other end by the latching device 32.

The invention claimed is:

1. A headband apparatus for a head-worn optical instrument, comprising a headband and a bow on which said optical instrument is mounted, said bow being mounted with both ends thereof at a middle region of said headband for swiveling about a swivel axis between a working position and a rest position, wherein fastening elements for releasably fastening at least one additional element are provided on said headband, said fastening elements form said swivel axis, said fastening elements extend outward through said ends of said bow, said additional element is formed by a latching device that permits swiveling of said bow between said working position and said rest position and locks said bow in these positions, and said latching device includes a latching disk which is connected to said fastening element in a rotationally fixed fashion and has a circularly arcuate guide slot in which there is guided a latching pin which is connected to said bow in a rotationally fixed fashion and engages in a latching fashion in said guide slot in said working position and/or said rest position of said bow.

2. The headband apparatus as claimed in claim 1, wherein said fastening elements are respectively fastened at a free end of an associated connecting lug, another end of said connecting lug permanently connected to said headband.

3. The headband apparatus as claimed in claim 1, wherein said additional element is mounted in a non-rotatable manner on said fastening element by positive engagement.

4. The headband apparatus as claimed in claim 1, wherein said latching device can be mounted on both of said fastening elements forming a swivel axis of said bow.

5. The headband apparatus as claimed in claim 1, wherein said fastening element passes through said latching disk and has a circumferential groove in which there engages in a locking position a locking element which is arranged in said latching disk and can be displaced transverse to said swivel axis into a release position in which it is disengaged from said circumferential groove.

6. The headband apparatus as claimed in claim 5, wherein said locking element is biased in the direction of said locking position.

7. A headband apparatus for a head-worn optical instrument, comprising a headband and a bow on which said optical instrument is mounted, said bow being mounted with both ends thereof at a middle region of said headband for swiveling about a swivel axis between a working position and a rest position, wherein fastening elements for releasably fastening at least one additional element are provided on said headband,
wherein said additional element is formed by a latching device that permits swiveling of said bow between said working position and said rest position and locks said bow in these positions, said latching device being mountable on both of said fastening elements forming a swivel axis of said bow, and
wherein said latching device includes a latching disk which is connected to said fastening element in a rotationally fixed fashion and has a circularly arcuate guide slot in which there is guided a latching pin which is connected to said bow in a rotationally fixed fashion and engages in a latching fashion in said guide slot in said working position and/or said rest position of said bow.

8. The headband apparatus as claimed in claim 7, wherein said fastening element passes through said latching disk and has a circumferential groove in which there engages in a locking position a locking element which is arranged in said latching disk and can be displaced transverse to said swivel axis into a release position in which it is disengaged from said circumferential groove.

9. The headband apparatus as claimed in claim 8, wherein said locking element is biased in the direction of said locking position.

* * * * *